(12) United States Patent
Mercado

(10) Patent No.: US 7,832,274 B1
(45) Date of Patent: Nov. 16, 2010

(54) SYSTEM AND METHOD FOR PNEUMATIC SCOUR DETECTION

(76) Inventor: Edward J. Mercado, #3 Lakewood La., Seabrook, TX (US) 77586

( * ) Notice: Subject to any disclaimer, the term of this patent is extended or adjusted under 35 U.S.C. 154(b) by 221 days.

(21) Appl. No.: 12/277,583

(22) Filed: Nov. 25, 2008

Related U.S. Application Data

(60) Provisional application No. 61/014,708, filed on Dec. 18, 2007.

(51) Int. Cl.
*G01N 29/00* (2006.01)
(52) U.S. Cl. ............................................ 73/594
(58) Field of Classification Search .............. 73/594, 73/597, 628, 861
See application file for complete search history.

(56) References Cited

U.S. PATENT DOCUMENTS

| | | | | |
|---|---|---|---|---|
| 3,617,996 A | * | 11/1971 | Herbert | 367/105 |
| 5,479,724 A | * | 1/1996 | Nahajski et al. | 33/719 |
| 5,753,818 A | * | 5/1998 | Mercado | 73/594 |
| 6,909,669 B1 | * | 6/2005 | Yankielun et al. | 367/131 |

* cited by examiner

*Primary Examiner*—Jewel Thompson
(74) *Attorney, Agent, or Firm*—Egbert Law Offices PLLC

(57) ABSTRACT

An apparatus for detecting scour conditions adjacent a pier has a pipe with a plurality of holes formed through a wall of the pipes in spaced relation to each other along a length of the pipe, a plurality of porous plugs affixed respectively in the plurality of holes, a plurality of tubes connected respectively to the plurality of porous plugs, a pump connected to the tubes for passing compressed air through the plurality of tubes to the plugs, and a monitor connected to the tubes for measuring a rate of pressure bleed-off from the plurality of tubes. The pipe extends in a vertical orientation adjacent to the bridge pier and extends into the earth adjacent the bridge pier. The plurality of porous plugs are spaced at equal intervals from each other.

20 Claims, 2 Drawing Sheets

SYSTEM AND METHOD FOR PNEUMATIC SCOUR DETECTION

RELATED U.S. APPLICATIONS

The present application claims priority from prior-filed U.S. Provisional Patent Application No. 61/014,708, filed on Dec. 18, 2007 and entitled "Pneumatic Scour Detection Instrument".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to devices for detecting scour around bridge foundations. More particularly, the present invention relates to dynamic devices for monitoring the condition of the river bed adjacent to bridge foundations and piers.

2. Description of Related Art Including Information Disclosed Under 37 CFR 1.97 and 37 CFR 1.98.

Total scour in a river channel occurs as a combination of three phenomena: General scour that may be influenced by contractions of the channel in the vicinity of a bridge, natural degradation of the channel due to active geologic processes, and local scour caused by local flow disturbances (primarily vortices) around piers and abutments. Most scour is at least in part a combination of two or more of these components, and it is difficult to separate the effects of each. Scour can occur in almost all soils, but the rate of scour is highest in cohesionless sands, gravels and silts; more moderate in dispersive clays; and slowest in non-dispersive clays and cemented granular soils. Given a flood, or series of floods, of sufficiently long duration, most soils will tend to scour to about the same depth. Scour depths of up to 60 feet have been inferred from the Salt River floods, and the reconstructed foundations have been designed with deep foundations to resist scour to these depths. Most of the replacement foundations have been deep, cylindrical drilled shafts, which are more streamlined than the driven pile sections that were originally used to support the bridges, since the circular shape of the drilled shaft will reduce the depth of local scour.

The scour in the immediate proximity of a bridge foundation is generally of more concern to the foundation engineer, however, than scour occurring far from piers or abutments. For example, for a footing bearing on the surface of cohesive soil with no frictional component of shear strength, the scouring of sediments producing a dip of 60 degrees in the surface of the sediments within a distance to the foundation equal to 75 percent of its width has no effect on ultimate bearing capacity, while the development of a scour zone with the same dip angle at and parallel to the edge of the footing reduces its bearing capacity by 30 percent. Such partial undercutting may not render the footing unsafe with respect to ultimate failure, but it may produce settlement, endangering the bridge's serviceability. A strong probability exists that scour-induced movements, which may be combinations of vertical and horizontal movements, in excess of 1.0 inch will not be tolerable by typical highway bridges. The settlement characteristics of the foundation will depend on the shape of the scour zone and the rate at which infilling (if any) occurs, and the type of infilled soil that may be deposited. It appears logical, therefore, that studies of scour that focus on the undermining of bridge foundations focus largely on the combined effects of general scour, degradation and local scour near foundations.

The effect of scour around bridge foundations has long been a consideration in bridge design, both from the point of view of the river hydraulics specialist and from that of the foundation engineer. Numerous bridge failures have been attributed to the undermining of interior piers or abutments by scour during floods. If the depth of scour in the vicinity of the pier or abutment exceeds the design limits, excessive movements of the foundation can occur, perhaps exceeding the service limit of the structure, even to the extent of completely undermining the foundation and producing collapse of the structure. Collapse from scour unfortunately often results in the loss of life but always causes serious traffic disruptions and expensive repairs. The Federal Government spends over $50,000,000 annually on the nation's primary road system for emergency bridge repairs, primarily from flood induced scour. Local and state agencies spend over twice that amount annually on emergency repairs to scour-damaged bridges.

A recent publication of the Federal Highway Administration cites the following recent statistics regarding the loss of bridges due to scour: In the spring floods of 1987, 17 bridges in New York and New England were destroyed or damaged by scour, and in 1985 73 bridges were destroyed by floods in West Virginia, Virginia and Pennsylvania, with damage being distributed approximately equally between piers and abutments. Severe floods in the western U.S. have also produced scour that have destroyed or made unserviceable major highway bridges, an example of which were recent floods on the Salt River in Arizona, which completely undermined pile-supported piers.

A major problem facing highway engineers is the lack of a simple, inexpensive scour detection device that can withstand the forces of floods and the impact of flood-borne debris. It is very important that a successful scour-detection device be able to provide real-time information to the highway engineers during a flood to warn of dangerous scour conditions.

Considerable serious bridge scour research has been conducted, but most of this research has been confined to the laboratory. This research has resulted in the development of methods, both semi-analytical and empirical, to predict scour depth, and these equations, among others, are currently used by bridge designers to predict scour depth for foundation design. Most of these methods were developed to apply to a particular type of scour (e.g., local scour at abutments), for particular ranges of Froude numbers in the scouring stream, and for particular foundation configurations and soil characteristics. Predicted scour depths vary according to these procedures, especially when applied outside of the range of parameters for which they were developed.

Some states, such as Minnesota, have begun systematic programs to catalog scour susceptible bridges and to outline rational procedures for further in-depth study, and in 1988, the Federal Highway Administration issued a technical advisory recommended the development and implementation of scour evaluation programs in all states. The acquisition of field data on scour, to augment data acquired from laboratory modeling, has been recognized as being essential to the improvement of the understanding and predictive capabilities regarding the estimation of the depth of scour, configurations of scour zones and the nature of re-deposited soils in the scour zone, if any. Such field studies require appropriate and reliable instrumentation.

Presently, there are a number of instruments that can be used to measure scour. The simplest and cheapest of all instruments are graduated poles and weighted lines that can be lowered to the river bed during and after a flood event from a bridge or from a boat. These devices are impractical in deep water and during high-velocity flow. Heat dissipation gages are fixed gages that consist of an assembly of electrical heaters and temperature sensors that are fastened together in a long rod, which is driven or jetted into the stream bed near a bridge pier. The wires leading from the heat dissipation gage assembly are routed to a central point on the bridge. During the flood event, an operator connects a battery to the sensors. The sensors above the river bed cool much faster than the sensors below the bed, such that the depth of scour at the location of the assembly is determined directly by comparing temperature records at various times. Resistance gages are used which include a metal sensing rod which is fixed directly on a pier or abutment with wires leading to a central point on the bridge. During a flood event, an operator connects a battery to the sensing rod to warm it. After a period of time, the battery is disconnected and the rod is allowed to cool. As the rod cools, it contracts much faster above the stream bed than below, and the strain gages on the rod can detect this differential contraction, allowing the operator to assess the depth of scour.

A fathometer can also be used so as to measure scour conditions. Fathometers are instruments which send and detect acoustic pulses electronically that are reflected from the river bottom and shallow sediment interfaces and accurately measure the depth of the scoured soil surface. Color fathometers are also available that process the reflected signal and allow for the interpretation of the depth and character of infilled soils. Fathometers are portable and can be used readily to investigate general scour patterns after a flood event, even in high velocity streams; however, they are problematical to use during a flood, since a boat carrying the fathometer must move from location to location.

Ground-penetrating radar can be used so as to penetrate the water column and soil strata immediately below the stream bed so as to provide a profile of the soils below the stream bed. The length of the electromagnetic radar waves at the frequency is about 0.4 meters at 80 MHz in water so as to give a resolution of about one foot. Higher frequencies can be used to improve resolution but with a severe penalty in sediment penetration. Since it is desirable to collect data on the presence and nature of infilled soils, high penetration is more important than high resolution. Ground-penetrating radar suffers from the disadvantage that it cannot be operated effectively and safely during a severe flood, except from the bridge. A technical disadvantage of this type of instrumentation is that the presence of a clay load or salt water in the stream severely attenuates the signal and produces poor resolution. As such, penetration of the water surface of more than about 25 feet would not be practically possible.

Side-scan sonar can be used so as to measure scour conditions by providing continuous acoustic pulses which are emitted at high frequency such that reflections are sensed by an acoustic transducer tuned to specific frequencies. Commercial side-scan sonar devices have rotating heads that allow for profiling of the soil surface away from the location of the instrument. It is usually operated by towing from a boat.

Seismic surveys are another technique of measuring scour conditions. Seismic surveys can be carried out in accordance with prior patent to the present inventor (U.S. Pat. No. 5,753, 818). This seismic technique is based upon installing an instrument access tube adjacent to and parallel to the bridge pier. A vertical array of hydrophones are inserted into this tube and record refracted events generated by a hammer blow on the pier which propagates down the pier and the water over the mud/soft sand over competent soil interface. The seismic energy is analyzed for deviations in first-break time to detect the low velocity mud/soft-sand zone/competent soil interface at the bottom of the scour zone. This seismic method requires installation of an access tube to hold the hydrophone array. It is possible that flood event debris could damage the tube and render it ineffective during the flood event.

It is an object of the present invention to provide an apparatus which measures scour depth profile dynamically.

It is another object of the present invention to provide a scour detection instrument which provides accurate sediment profile resolution in all types of sediments and waters.

It is another object of the present invention to provide a scour detection instrument which is portable.

It is another object of the present invention to provide a scour detection instrument which is of low cost.

It is a further object of the present invention to provide a scour detection instrument which is very reliable and which can perform under extreme flood conditions.

It is still another object of the present invention to provide a scour detection instrument which is easy to operate.

These and other objects and advantages of the present invention will become apparent from a reading of the attached specification and appended claims.

BRIEF SUMMARY OF THE INVENTION

The present invention is an apparatus for detecting scour conditions adjacent to a bridge pier comprising a pipe having a wall and an interior passageway. A plurality of porous plugs are affixed at vertical intervals in the wall of the pipe so as to open to an exterior of the wall of the pipe. A plurality of tubes are connected respectively to the plurality of plugs and extend from the plurality of plugs through the interior passageway of the pipe to an end of the pipe. A pump is connected to the plurality of tubes so as to pass compressed air through the plurality of tubes into the plurality of plugs. A monitoring means is connected to the plurality of tubes. The monitoring means serves to measure a rate of pressure bleed-off from the plurality of tubes through the plurality of plugs relative to a position of the plug in the water.

In the present invention, the pipe should be a rigid steel pipe. The pipe can be installed vertically against a bridge pier. The pipe will penetrate to a depth equal to the depth of the footing of the bridge pier. Preferably, the steel pipe will be streamlined on the upstream face thereof so as to minimize turbulence in the water. The steel pipe can be affixed to the upstream side of the pier.

The porous and permeable plugs are embedded and sealed in the wall of the pipe. These plugs are positioned at uniform vertical intervals along the length of the pipe. The porosity of the plugs is controlled so as to allow fluid to pass therethrough while resisting the passage of clay-sized particles. The plug will have an end which is flush with the exterior surface of the pipe.

The plurality of tubes will extend to the surface above the water. The tubes are connected to the plugs interior of the pipe. These tubes extend through the pipe to the surface. These tubes allow a fluid to be pumped therethrough.

In the present invention, the pump mechanism allows high pressure fluid to be introduced to the tubes. Ideally, this pump will pass compressed air into the tubes. The monitoring means can measure both the pressure required to initiate fluid flow through the plug and the rate of fluid flow as a function of pressure so as to indicate whether the plug is in contact with competent soil or open to water. The monitoring of the change of air pressure bleed-off will define the depth of the scour relative to the position on the pipe.

The present invention is also a method of measuring scour conditions adjacent a pier. The method of the present invention comprises the steps of: (1) forming a pipe having a plurality of porous plugs extending through a wall of the pipe so as to have an end adjacent an exterior wall of the pipe; (2) connecting a plurality of tubes respectively to the plurality of pipes; (3) placing the pipe into the earth adjacent the pier such that at least one of the porous plugs is in the earth; (4) pumping a fluid through the plurality of tubes and the plurality of porous plugs such that the fluid is directly outwardly of the plurality of porous plugs; and (5) measuring a rate of pressure bleed-off of the fluid through the plurality of porous plugs.

In the method of the present invention, the step of measuring includes measuring a pressure to initiate fluid flow through the plurality of porous plugs and measuring a rate of fluid flow through the plurality of porous plugs as a function of the pressure applied to the fluid. The step of placing the pier includes extending the pipe vertically such that a portion of the pipe extends through water above the earth adjacent the pier. The step of placing comprises driving the pipe into the earth adjacent an upstream side of the pier such that a lower end of the pipe is at a depth in the earth approximately equal to a depth that the pier extends into the earth. The plurality of tubes extend through an interior passageway of the pipe so as to extend outwardly of an upper end of the pipe. The upper end of the pipe is above a surface of a body of water above the earth.

DETAILED DESCRIPTION OF THE INVENTION

Figure 1:
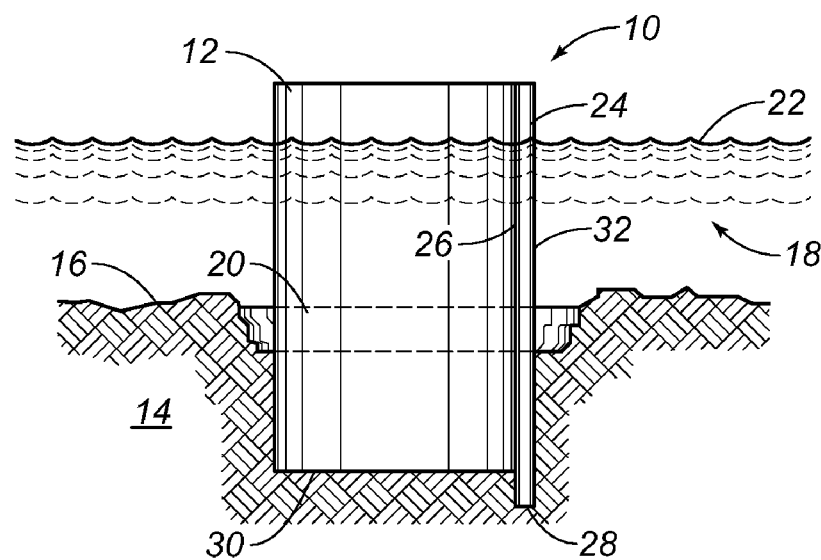
FIG. 1 is a diagrammatic illustration of the scour detection instrument of the present invention as applied to a bridge pier within a river bed.

Referring to FIG. 1, there is shown at 10 the scour detection instrument in accordance with the teachings of the present invention. As shown in FIG. 1, a bridge pier 12 is positioned in competent soil 14 below the water bottom 16 of river 18. A scour zone 20 is located in the river 18 at the water bottom 16 adjacent to pier 12. The scour zone 20 is located above competent soil 14. The pier 12 will extend above the top of the water surface 22.

The scour detection instrument 10 comprises, in part, a steel pipe 24 which is affixed to the upstream side 26 of pier 12. The steel pipe 24 extends along the side of the pier 12 so as to have a bottom 28 extending at or below the footing 30 of the pier 12 within the competent soil 14. As can be seen, the pipe 24 extends vertically along the bridge pier 12. The upstream side 32 of pipe 24 can be suitably streamlined so as to minimize turbulence of the interaction of the river 18 against the pier 12.

Figure 2:
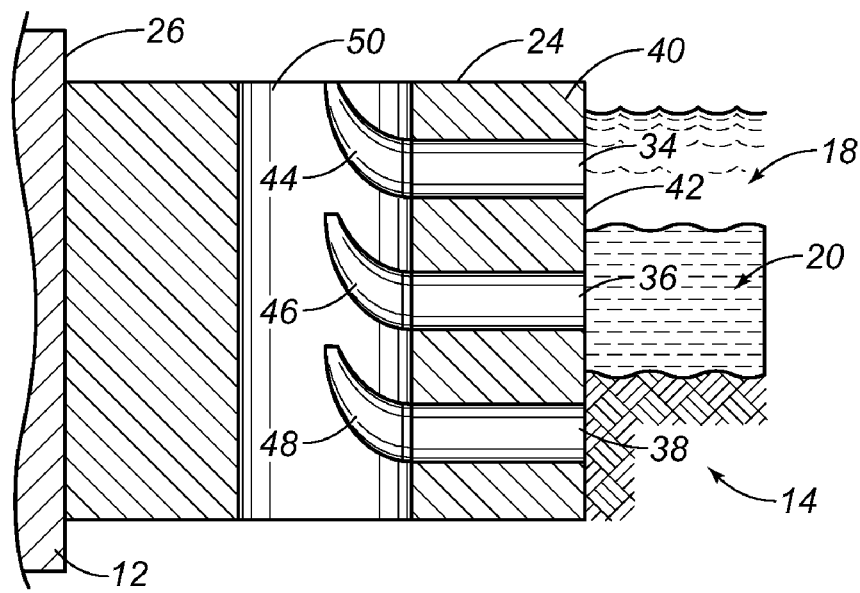
FIG. 2 is a detailed view showing the placement of the plugs in the wall of the pipe and the tubes which extend therefrom.

In FIG. 2, it can be seen how the permeable plugs 34, 36 and 38 are sealed within the wall 40 of pipe 24. Each of the plugs 34, 36 and 38 are embedded in the wall 40 of pipe 24. The plugs 34, 36 and 38 are positioned at uniform intervals along the length of pipe 24. The porosity of each of the plugs 34, 36 and 38 is controlled so as to allow fluid to pass therethrough while being impermeable to the passage of clay-sized particles. Each of the plugs 34, 36 and 38 will have an outer end flush with the exterior surface 42 of pipe 24. Tubes 44, 46 and 48 are affixed, respectively, to the interior ends of plugs 34, 36 and 38. The tubes 44, 46 and 48 are rubber tubes which extend through the interior passageway 50 of pipe 24 to the surface of the pipe 24. The tubes 44, 46 and 48 allow a fluid to be pumped therethrough and outwardly through the respective plugs 34, 36 and 38.

In FIG. 2, the pipe 24 is affixed against the wall 26 of pier 12. The plug 34 has its end emerging in water layer 18. Plug 36 emerges in the mud layer 20. Finally, plug 38 emerges in the competent soil layer 14.

Figure 3:
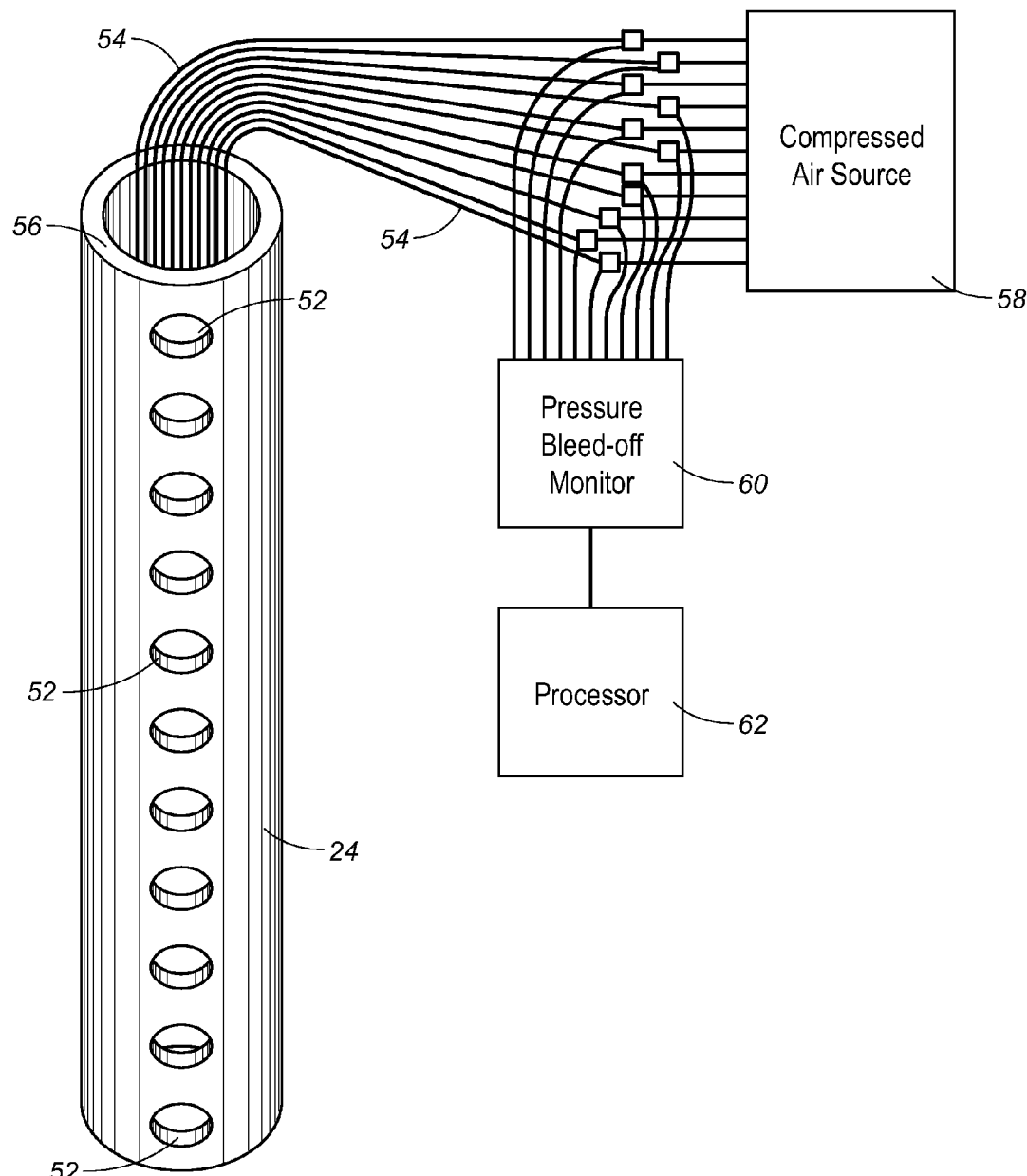
FIG. 3 is a diagrammatic illustration of the instrumentation associated with the scour detection instrument of the present invention.

In FIG. 3 the operation of the present invention is illustrated diagrammatically. The pipe 24 has a suitable length with a plurality of plugs extending vertically along the wall of pipe 24. A total of eleven (11) plugs 52 are illustrated in FIG. 3 as extending along the length of the pipe 24. Tubes 54 correspond to each of the plugs 52 and are connected to each of the plugs in the manner described in FIG. 2. Tubes 54 will extend outwardly beyond the upper end 56 of pipe 24. Each of the tubes 54 are connected to a source of compressed air 58. As such, compressed air can be delivered into each of the tubes 54 for passage into and through the plugs 52. So as to monitor the bleed-off of the pressure in each of the tubes 54, a pressure bleed-off monitor 60 is interactively connected to each of the respective tubes 54. A processor 62 can be connected to the pressure bleed-off monitor 60 so as to provide a humanly perceivable indication of the scour condition of the river bed.

The present invention provides an instrument which provides scour instrumentation based upon the difference in air or fluid flow through a vertical array of porous and permeable plugs 52 embedded inside a rugged steel pipe 24 installed adjacent to a bridge pier 26 where the plugs 52 are expelling air against the water versus mud/soft sand versus competent soil interfaces. As can be seen in the previously described figures, a series of porous and permeable plugs 52 are positioned at uniform vertical intervals along the pipe 24. Each plug is internally fastened to a tube 54 leading to the surface through which air or water can be pumped. The porosity of the plugs 52 is controlled to allow passage of air or water through it in either direction, but is impermeable to the passage of clay-sized particles suspended in the river water. The rate of pressure bleed-off at any individual plug will indicate whether the external face of the permeable plug 52 is in contact with either water, mud/soft sand, or competent soil. The mud/soft-sand area should offer approximately the same resistance to flow through the plug as water. This would indicate the presence of scour at that level. When the external surface of the plug 52 is in contact with competent soil (such as that shown by plug 38 in FIG. 2), the soil 14 will provide resistance to fluid flow significantly greater than water 18. Thus, both the pressure required to initiate fluid flow through each plug and the rate that fluid does flow as a function of pressure will identify whether the plug is in contact with competent soil 14 or open to water 18. The impermeable nature of the plug to the clay-sized fraction of sediments prevents the plug from becoming clogged with these fines by inadvertent back-flow through the plug.

Because of the construction of the instrument 10 from a heavy duty steel pipe with porous plugs made of hard material, the instrument 10 will be able to operate under severe flood conditions. During a flood event, as scour increases in depth, progressively deeper porous plugs will be exposed to water as the surrounding competent soil is eroded away. Gravel and debris will not seal the exposed surface of the porous plugs 52 so that the compressed air in the tube 54 will be able to bleed into the water 18. The change in air pressure bleed rate is easily monitored at the surface for each individual porous plug. This provides the information necessary to define the depth of scour.

Flood-borne debris routinely collects into large "birds nests", or rafts around piers, and will not adversely affect the operation of the scour detection instrument 10 because the permeable plugs 52 are small in diameter (approximately one-half inch) and the debris will not seal them off from the water. The instrument will remain in place and will be functional until such time as the pier itself is destroyed by the flood. Sensitivity of the instrument to measure scour depth is controlled by the vertical spacing of the permeable plugs in the pipe wall.

The present invention achieves many advantages. The scour detection instrument of the present invention is very simple. This simplicity translates into low cost and ruggedness. By using heavy steel piping, similar to drill stem tubing in oil well drilling, the ruggedness of the in water/soil part of the instrument can be controlled. With the pipe fastened directly to the upstream side of the bridge pier, it will not be swept away by flood debris. By inserting strong, porous permeable plugs flush with the external surface of the pipe, the pipe can be battered down for installation, and the debris collecting around the pier will not seal the plug face to a point where, under pressure, the testing fluid cannot enter the water layer.

The system of the present invention can be easy to install during new bridge construction. On existing bridges, the pipe can be battered down. Battering down the pipe is the preferred method of emplacement so as to effectively seal the faces of the porous plugs against the competent soil. The system provides a cost advantage since the pipe needs only be permanently implanted at abridge site. The system can be made vandal resistant by placing the pneumatic connection points at inaccessible places under the bridge span, or even by providing a lockable box permanently installed on top of the pipe to contain the pneumatic hoses leading to the individual permeable plugs. The system can be highly automated by placing the instruments under program control by a PC-type computer. The analysis of the data to measure depth-of-scour also can be computerized by measuring changes in pressure bleed-off rates between pairs of permeable plugs. When potentially dangerous scour conditions are sensed, the computer could activate a radio signal to a local center warning them of a scour alert.

The foregoing disclosure and description of the invention is illustrative and explanatory thereof. Various changes in the details of the illustrated construction can be made within the scope of the present invention. The present invention should only be limited by the following claims and their legal equivalents.

I claim:

1. An apparatus for detecting scour conditions adjacent a pier comprising:
    a pipe having a plurality of holes formed through a wall of said pipe, said plurality of holes being in spaced relation to each other and extending along a length of said pipe;
    a plurality of porous plugs affixed respectively in said plurality of holes;
    a plurality of tubes connected respectively to said plurality of porous plugs;
    a pumping means connected to said plurality of tubes for passing compressed air through said plurality of tubes to said plurality of porous plugs; and
    a monitoring means connected to said plurality of tubes for measuring a rate of pressure bleed-off from said plurality of tubes.

2. The apparatus of claim 1, said pipe having an interior passageway, said plurality of tubes extending through said interior passageway.

3. The apparatus of claim 1, said pipe extending in a vertical orientation, said plurality of holes having a longitudinal axis extending horizontally.

4. The apparatus of claim 1, said plurality of porous plugs being spaced at equal intervals from each other.

5. The apparatus of claim 1, each of said plurality of porous plugs opening to an exterior surface of said pipe.

6. The apparatus of claim 1, each of said plurality of porous plugs having an end that is flush with said exterior surface of said pipe.

7. The apparatus of claim 1, each of said plurality of porous plugs having a porosity suitable for allowing a passage of a fluid therethrough and for preventing a flow of clay-sized particles therethrough.

8. The apparatus of claim 2, said plurality of tubes extending outwardly of an upper end of said pipe.

9. The apparatus of claim 1, said monitoring means for measuring a pressure required to initiate fluid flow through each of the plurality of porous plugs and a rate of fluid flow as a function of the pressure.

10. A system of detecting scour conditions comprising:
    a pier embedded in the earth at a bottom of a body of water;
    a pipe positioned adjacent and pier, said pipe extending into the earth and upwardly therefrom through the body of water, said pipe having a plurality of holes formed through a wall of said pipe, said plurality of holes being in spaced relation to each other and extending along a length of said pipe;
    a plurality of porous plugs affixed respectively in said plurality of holes;
    a plurality of tubes connected respectively to said plurality of porous plugs;
    a pumping means connected to said plurality of tubes for passing a fluid through said plurality of tubes to said plurality of porous plugs; and
    a monitoring means connected to said plurality of tubes for measuring a rate of pressure bleed-off from said plurality of tubes.

11. The system of claim 10, said pipe having an interior passageway, said plurality of tubes extending through said interior passageway.

12. The system of claim 1, said pipe extending in a vertical orientation, said plurality of holes having a longitudinal axis extending horizontally.

13. The apparatus of claim 10, said pipe extending into the earth for a distance approximately equal to a depth that said pier is embedded in the earth.

14. The system of claim 10, said pipe being positioned at an upstream side of said pier.

15. The system of claim 10, said plurality of porous plugs being spaced at equal intervals from each other, at least one of said plurality of porous plugs opening to an exterior surface of said pipe that extends into the earth, another of said plurality of porous plugs opening to an exterior surface of said pipe that is in said body of water above the earth.

16. A method of measure scour conditions adjacent a pier comprising:
- forming a pipe having a plurality of porous plugs extending through a wall of said pipe so as to have an end adjacent an exterior wall of said pipe;
- connecting a plurality of tubes respectively to said plurality of porous plugs;
- placing said pipe into the earth adjacent said pier such that at least one of said plurality of porous plugs is in the earth;
- pumping a fluid through said plurality of tubes and said plurality of porous plugs such that the fluid is directed outwardly of said plurality of porous plugs; and
- measuring a rate of pressure bleed-off of the fluid through said plurality of porous plugs.

17. The method of claim 16, said step of measuring comprising:
- measuring a pressure to initiate fluid flow through said plurality of porous plugs; and
- measuring a rate of fluid flow through said plurality of porous plugs as a function of the pressure applied to the fluid.

18. The method of claim 16, the step of placing said pipe comprising:
- extending said pipe vertically such that a portion of said pipe extends through water above the earth adjacent the pier.

19. The method of claim 16, the step of placing comprising:
- driving said pipe into the earth adjacent an upstream side of the pier such that a lower end of said pipe is at a depth in the earth approximately equal to a depth that the pier extends into the earth.

20. The method of claim 16, said plurality of tubes extending through an interior passageway of said pipe so as to extend outwardly of an upper end of said pipe, said upper end of said pipe being above a surface of said body of water above the earth.

* * * * *